(12) United States Patent
Daglow (10) Patent No.: US 8,849,418 B2
(45) Date of Patent: Sep. 30, 2014

(54) ANCHOR SLEEVE FOR IMPLANTABLE LEAD

(75) Inventor: Terry Douglas Daglow, Bonham, TX (US)

(73) Assignee: Greatbatch Ltd., Clarence, NY (US)

( * ) Notice: Subject to any disclaimer, the term of this patent is extended or adjusted under 35 U.S.C. 154(b) by 403 days.

(21) Appl. No.: 13/045,947

(22) Filed: Mar. 11, 2011

(65) Prior Publication Data

US 2012/0232626 A1  Sep. 13, 2012

(51) Int. Cl.
| | |
|---|---|
| A61N 1/05 | (2006.01) |
| A61N 1/36 | (2006.01) |
| A61M 39/02 | (2006.01) |
| A61M 5/14 | (2006.01) |

(52) U.S. Cl.
CPC ............... *A61N 1/05* (2013.01); *A61N 1/3605* (2013.01); *A61N 1/0558* (2013.01); *A61M 2039/0223* (2013.01); *A61M 2039/0261* (2013.01); *A61M 2005/1416* (2013.01)
USPC ........................................................ 607/116

(58) Field of Classification Search
None
See application file for complete search history.

(56) References Cited

U.S. PATENT DOCUMENTS

| | | | |
|---|---|---|---|
| 4,553,961 A | 11/1985 | Pohndorf et al. | |
| 4,672,979 A | 6/1987 | Pohndorf | |
| 5,484,445 A | 1/1996 | Knuth | |
| 5,584,874 A | 12/1996 | Rugland et al. | |
| 5,843,146 A | 12/1998 | Cross, Jr. | |
| 5,876,373 A * | 3/1999 | Giba et al. | 604/95.04 |
| 6,134,477 A | 10/2000 | Knuteson | |
| 7,831,313 B2 | 11/2010 | Lauro | |
| 2007/0050005 A1* | 3/2007 | Lauro | 607/126 |
| 2007/0078399 A1 | 4/2007 | Olson | |
| 2009/0125058 A1* | 5/2009 | Bodner et al. | 606/232 |
| 2009/0177041 A1* | 7/2009 | Stefanchik et al. | 600/146 |
| 2010/0274336 A1 | 10/2010 | Nguyen-Stella et al. | |

OTHER PUBLICATIONS

Violette M. Renard, M.D., and Richard B. North, M.D., Prevention of Percutaneous Electrode Migration in Spinalcord Stimulation by a Modification of the Standardimplantation Technique, Apr. 2006.

* cited by examiner

*Primary Examiner* — Brian T Gedeon
*Assistant Examiner* — Ankit Tejani
(74) *Attorney, Agent, or Firm* — Michael P. Horvath (57) ABSTRACT

An anchor sleeve for securing a therapy delivery element, such as a stimulation lead or catheter, within a living body, that includes an inner sleeve with pre-formed locations of weakness that facilitate localized deformation. The anchor includes a deformable outer sleeve with a primary lumen extending along an axis. The outer surface of the outer sleeve includes a plurality of suture grooves oriented generally concentric to the axis. The inner sleeve includes a plurality of beams connected at deflection regions arranged around a secondary lumen. The inner sleeve is located in the primary lumen adjacent to the suture grooves so that the secondary lumen is generally concentric with the primary lumen. A plurality of locations of weakness are preformed in each of the beams to facilitate localized deformation in response to a radially inward force applied around the suture grooves by a suture material.

22 Claims, 12 Drawing Sheets

ANCHOR SLEEVE FOR IMPLANTABLE LEAD

FIELD

The present disclosure relates to an anchor sleeve for securing a therapy delivery element, such as a stimulation lead or catheter, within a living body. The anchor includes an inner sleeve with pre-formed locations of weakness that facilitate localized deformation around the therapy delivery element.

BACKGROUND

Implantable medical devices are used for a wide variety of medical conditions, such as for example, cardiac pace making, cardiac rhythm management, treatments for congestive heart failure, implanted defibrillators, and neurostimulation. Neurostimulation encompasses a wide range of applications, such as for example, pain control, nervous tremor mitigation, incontinent treatment, epilepsy seizure reduction, and vagus nerve stimulation for clinical depression.

These implantable medical devices generally include an implanted pulse generator that generates electrical pulses or signals that are transmitted to a targeted tissue or nerves through a therapy delivery element, such as a lead with electrodes. Controlled placement of the therapy delivery element is required for improved therapeutic efficacy or reduced side effects. Retaining the implanted therapy delivery element in the desired location also creates difficulties because the location may change over time as the patient moves. A variety of anchors are available to prevent the therapy delivery element from migrating away from a specifically selected stimulation site.

U.S. Pat. No. 4,553,961 (Pohndorf et al.) discloses a typical suture sleeve with an outer elastomeric sleeve and an inner gripping structure. The lead is inserted though a lumen in the anchor. The gripping structure is radially compressed by tying of sutures around the suture sleeve.

Clinicians inserting and anchoring therapy delivery elements typically prefer to perform the procedure rapidly, in a minimally invasive manner, and fix the therapy delivery element in a manner that reduces the opportunity for the therapy delivery element to migrate if practicable. Examples of some previous anchors are shown in U.S. Pat. No. 6,134,477 "Adjustable Medical Lead Fixation System" by Knuteson (Oct. 17, 2000); U.S. Pat. No. 5,484,445 "Sacral Lead Anchoring System" by Knuth (Jan. 16, 1996); and, U.S. Pat. No. 5,843,146. "Adjustable Medical Lead Anchor" by Cross, Jr. (Dec. 1, 1998).

BRIEF SUMMARY

The present disclosure relates to an anchor sleeve for securing a therapy delivery element, such as a stimulation lead or catheter, within a living body. The anchor includes an inner sleeve with pre-formed locations of weakness that facilitate localized deformation around the therapy delivery element.

In one embodiment, the anchor includes a deformable outer sleeve with a primary lumen extending along an axis. The outer surface of the outer sleeve includes a plurality of suture grooves oriented generally concentric to the axis. The inner sleeve includes a plurality of beams connected at deflection regions arranged around a secondary lumen. The inner sleeve is located in the primary lumen adjacent to the suture grooves so that the secondary lumen is generally concentric with the primary lumen. A plurality of locations of weakness are preformed in each of the beams to facilitate localized deformation in response to a radially inward force applied around the suture grooves by a suture material.

The outer sleeve typically includes distal portions extending beyond the inner sleeve. In one embodiment, at least a portion of the primary lumen includes grooves adapted to receive a medical adhesive. The outer sleeve optionally includes one or more fill ports adapted to direct a medical adhesive to at least the primary lumen. The at least one fill port preferably includes a connector to receive a dispenser containing a medical adhesive. The outer sleeve is preferably constructed from an elastomeric material.

The inner sleeve is made from a material that plastically or elastically deforms in response to the radially inward force, such as for example, a thermoplastic material, stainless steel, or Nitinol. The locations of weakness are typically discontinuities in the beams, such as slits, holes, recesses, regions thinning, or a combination thereof. The localized deformation can be one or more of bending, twisting, elongation, compression, or a combination thereof.

The present disclosure is also directed to a neurostimulation system including an implantable pulse generator and a therapy delivery element. The therapy delivery element includes a proximal end adapted to electrically couple with the implantable pulse generator, and a distal end with a plurality of electrodes electrically coupled to the implantable pulse generator. The present anchor is provided to secure the therapy delivery element in a desired location within a living body.

The present disclosure is also directed to a method of securing a therapy delivery element at a desired location within a living body. The method includes the steps of inserting the therapy delivery element through lumens of an anchor. The anchor includes an outer sleeve with a primary lumen and an inner sleeve with a secondary lumen located within the primary lumen. The primary lumen is generally concentric with the secondary lumen. The anchor is slid along the therapy delivery element to the desired location. A suture material is wrapped around at least one suture groove aligned with the inner sleeve that is formed in an outer surface of the outer sleeve. A radially inward force is applied at the suture groove by tensioning the suture material. The radially inward force creates localized deformation at locations of weakness preformed in beams of the inner sleeve. The inner sleeve compressively engages the therapy delivery element. The suture material is used to attach the anchor to the desired location within the living body.

The present method optionally includes the steps of coupling a dispenser containing a medical adhesive to a fill port on the outer sleeve and delivering the medical adhesive to at least the primary lumen. The medical adhesive is preferably delivered to at least the primary lumen before the step of applying the radially inward force at the suture groove.

The present disclosure is also directed to a method of implanting a neurostimulation system within a living body. The method includes the steps of implanting an implantable pulse generator within the living body. Electrodes at a distal end of a therapy delivery element are positioned at a target location within the living body. A proximal end of the therapy delivery element is inserted into lumens in the present anchor. The anchor is slide along the therapy delivery element to a desired location. A suture material is wrapped around at least one suture groove aligned with the inner sleeve that is formed in an outer surface of the outer sleeve. A radially inward force is applied at the suture groove by tensioning the suture material. The radially inward force creates localized deformation at locations of weakness preformed in beams of the inner sleeve. The inner sleeve compressively engages the therapy delivery element. The suture material attaches the anchor to tissue within the living body. The proximal end of the therapy delivery element is electrically coupled to the implantable pulse generator.

DETAILED DESCRIPTION OF SOME EMBODIMENTS

The description that follows relates to a spinal cord stimulation (SCS) system. However, it is to be understood that the while the present disclosure lends itself well to applications in SCS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

In another embodiment, one or more of the therapy delivery elements may be a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be an electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, extensions for any of the above, or combinations thereof. "Target tissue site" refers generally to the target site for implantation of a therapy delivery element, regardless of the type of therapy.

Figure 1A:
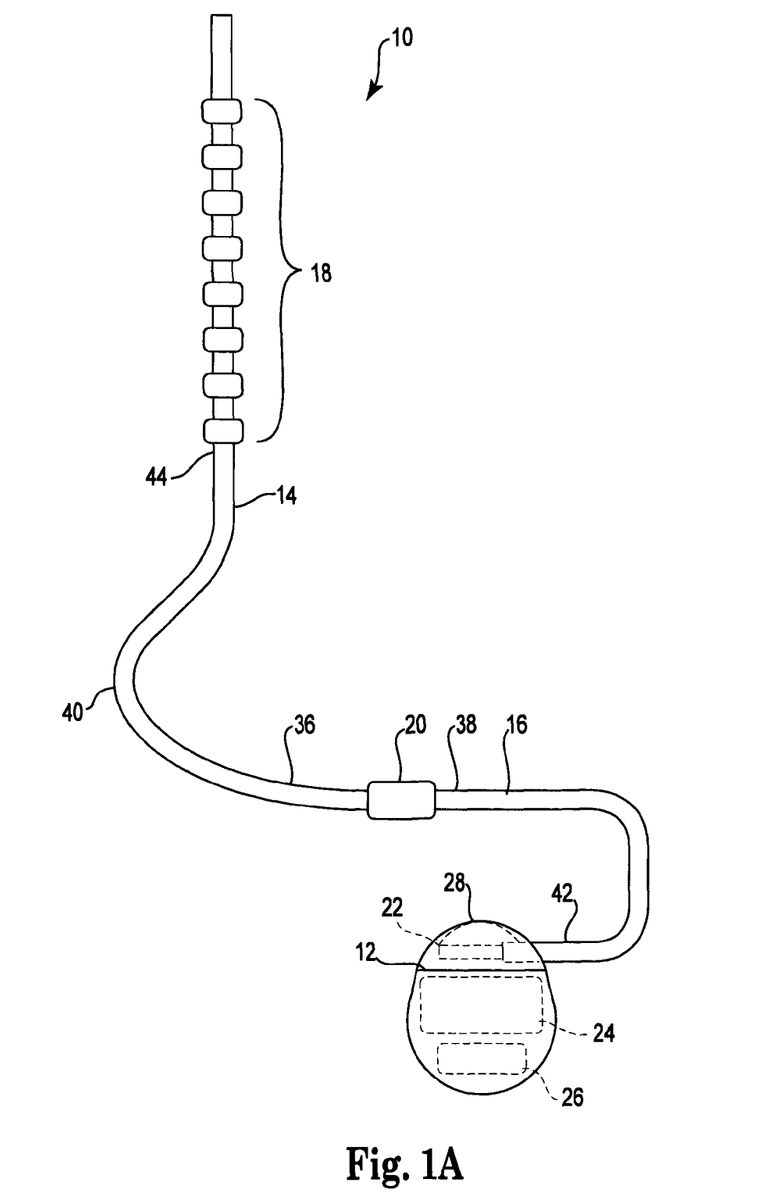
FIG. 1A is a schematic illustration of a therapy delivery system.

FIG. 1A illustrates a generalized therapy delivery system 10 that may be used in spinal cord stimulation (SCS), as well as other stimulation applications. The therapy delivery system 10 generally includes an implantable pulse generator 12, an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10 (See e.g., FIG. 1C).

The therapy delivery element 14 includes elongated body 40 having a proximal end 36 and a distal end 44. The elongated body 40 typically has a diameter of between about 0.03 inches to 0.07 inches and a length within the range of 30 cm to 90 cm for spinal cord stimulation applications. The elongated body 40 may be composed of a suitable electrically insulative material, such as, a polymer (e.g., polyurethane or silicone), and may be extruded from as a uni-body construction.

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector assembly 22 associated with housing 28. Alternatively, the proximal end 36 of the therapy delivery element 14 can be electrically coupled directly to the connector 20.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 is protected from the body tissue and fluids. The connector assembly 22 is disposed in a portion of the housing 28 that is, at least initially, not sealed. The connector assembly 22 carries a plurality of contacts that electrically couple with respective terminals at proximal ends of the therapy delivery element 14 or extension lead 16. Electrical conductors extend from the connector assembly 22 and connect to the electronic subassembly 24.

Figure 1B:
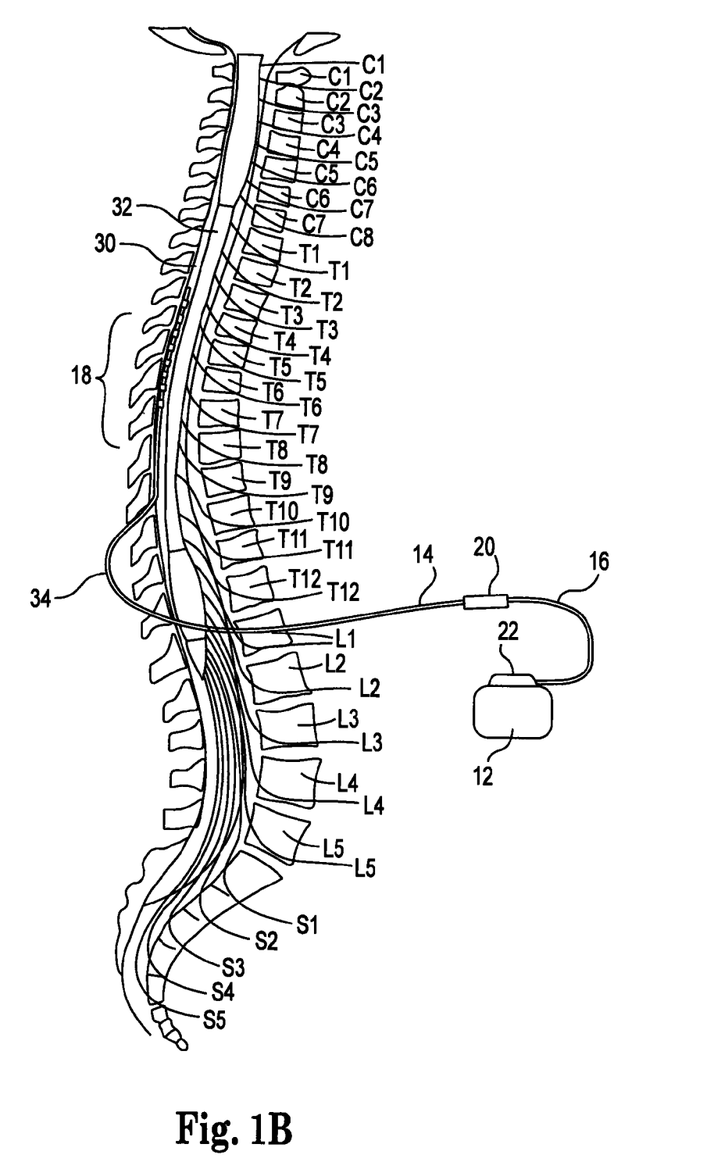
FIG. 1B is a schematic illustration of an environment for a therapy delivery system in accordance with an embodiment of the present disclosure.

FIG. 1B illustrates the therapy delivery element 14 implanted in the epidural space 30 of a patient in close proximity to the dura, the outer layer that surrounds the spinal cord 32, to deliver the intended therapeutic effects of spinal cord electrical stimulation. The target stimulation sites may be anywhere along the spinal cord 32, such as for example proximate the sacral nerves.

Figure 1C:
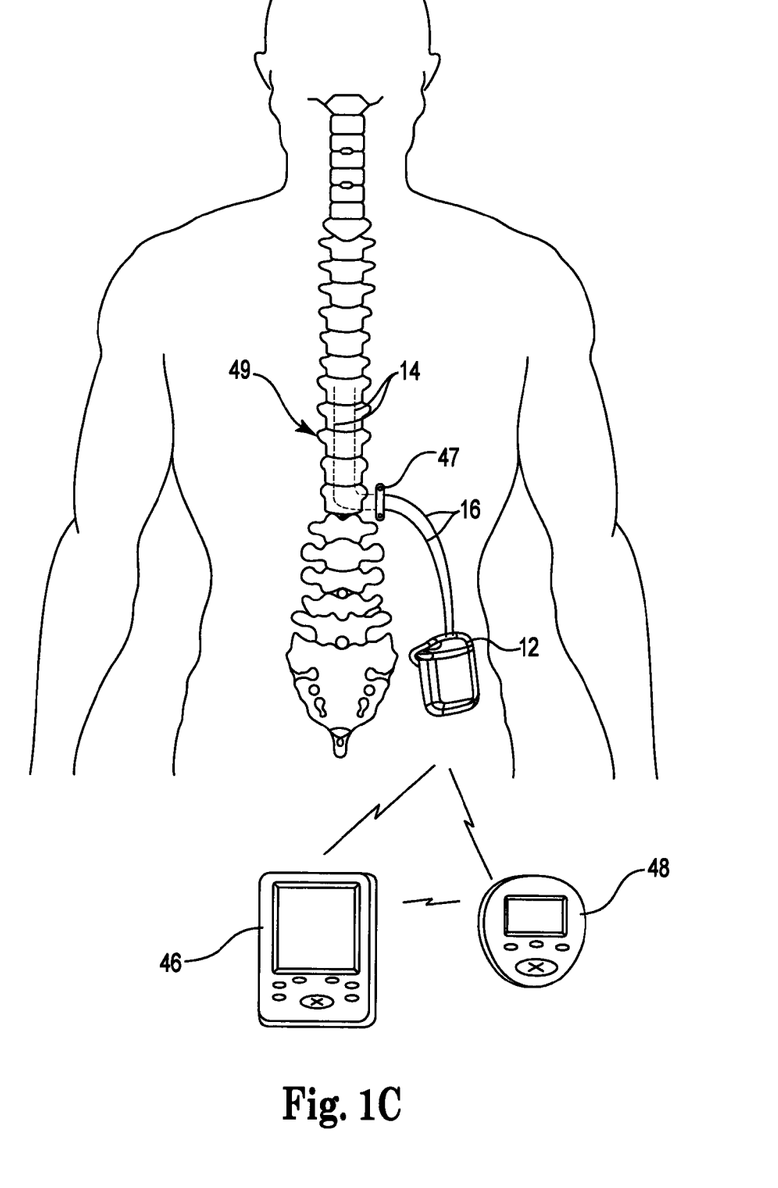
FIG. 1C is an alternate illustration of the environment for an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 1C. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector assembly 22 of the implantable pulse generator 12, since different manufacturers use different connectors at the ends of their stimulation leads and are not always compatible with the connector assembly 22.

As illustrated in FIG. 1C, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 48, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Since the implantable pulse generator 12 is located remotely from target location 49 for therapy, the therapy delivery element 14 and/or the extension leads 16 is typically routed through a pathways subcutaneously formed along the torso of the patient to a subcutaneous pocket where the implantable pulse generator 12 is located. As used hereinafter, "lead" and "lead extension" are used interchangeably, unless content clearly dictates otherwise.

The therapy delivery elements 14 are typically fixed in place near the location selected by the clinician using anchor 47, such as in the epidural space 30. The anchor 47 can be positioned on the therapy delivery element 14 in a wide variety of locations and orientations to accommodate individual anatomical differences and the preferences of the clinician. The anchor 47 may then be affixed to tissue using fasteners, such as for example, one or more sutures, staples, screws, or other fixation devices. The tissue to which the anchor 47 is affixed may include subcutaneous fascia layer, bone, or some other type of tissue. Securing the anchor 47 to tissue in this manner prevents or reduces the chance that the therapy delivery element 14 will become dislodged or will migrate in an undesired manner.

Figure 2:
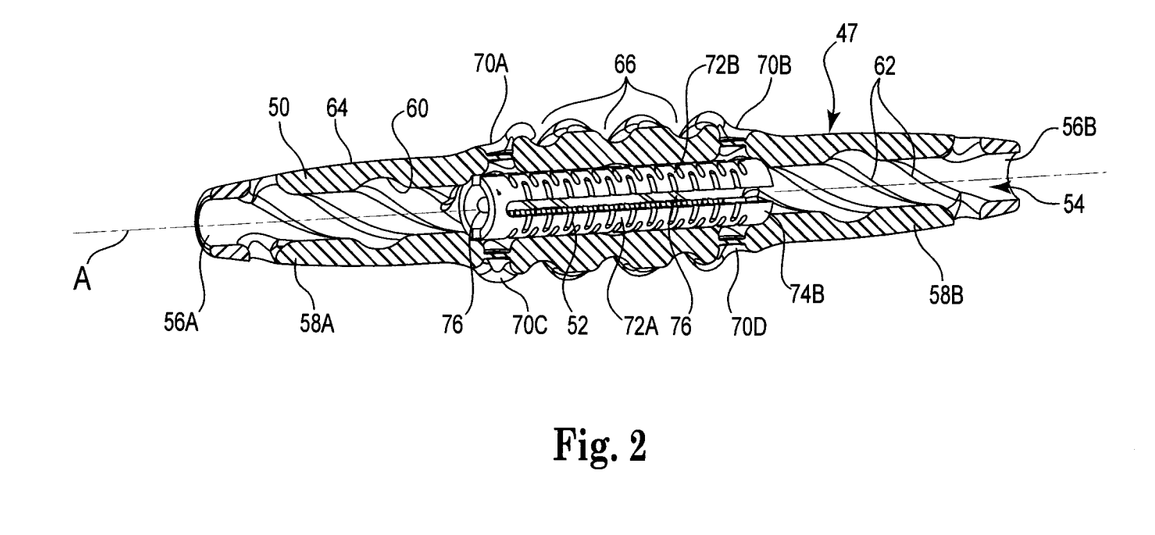
FIG. 2 is a sectional view of an anchor for a therapy delivery element in accordance with an embodiment of the present disclosure.

FIG. 2 is a sectional view of outer sleeve 50 revealing inner sleeve 52 of anchor 47 in accordance with an embodiment of the present disclosure. Outer sleeve 50 includes primary lumen 54 extending along axis A from first opening 56A to second opening 56B ("56"). The outer sleeve 50 preferably has distal portions 58A, 58B that extend beyond the inner sleeve 52.

In the illustrated embodiment, inner surface 60 of the primary lumen 54 includes one or more spiral grooves 62, used to channel medical adhesive, as will be discussed further below. Outer surface 64 includes one or more suture grooves 66 around which suture material 68 is wrapped (see FIG. 8) to compress the anchor 47 onto a therapy delivery element 14. The suture grooves 66 are preferably axially aligned with the inner sleeve 52 along axis A. The outer sleeve 50 optionally includes one or more fill ports 70A, 70B, 70C, 70D ("70") used to direct a medical adhesive (see FIG. 7) to at least primary lumen 54. The outer sleeve 52 is preferably injection molded using elastomeric material, such as for example, medical grade silicone.

Figure 3:
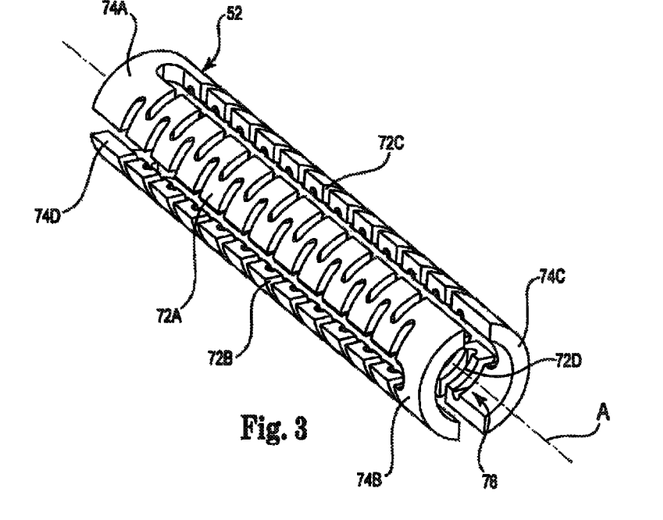
FIG. 3 is a perspective view an inner sleeve for the anchor of FIG. 2.

FIG. 3 is a perspective view of the inner sleeve 52 separated from the outer sleeve 50. The inner sleeve 52 includes a series of beams 72A, 72B, 72C, 72D ("72") connected by deflection region 74A, 74B, 74C, 74D ("74"). The beams 72 are configured in a serpentine pattern so that each beam 72 has multiple deflection regions 74. For example, beam 72A is attached to the inner sleeve 52 at deflection regions 74A, 74B. In the illustrate illustrated embodiment, deflection region 74A is oriented and acts generally perpendicular to deflection region 74B.

The number of beams 72 can vary depending on the application. In the illustrated embodiment the beams 72 are configured with secondary lumen 76 also extending along axis A. The secondary lumen 76 of the inner sleeve 52 and the primary lumen 54 of the outer sleeve 50 are preferably both positioned concentrically relative to the axis A.

The inner sleeve 52 can be made from a variety of plastically and/or elastically deformable materials, such as for example, nylon, stainless steel, Nitinol, and the like. In another embodiment, the inner sleeve 52 is treated to be radiopaque. In one embodiment, the inner sleeve 52 is stainless steel formed by wire electro-discharge machining processes.

Figure 4A:
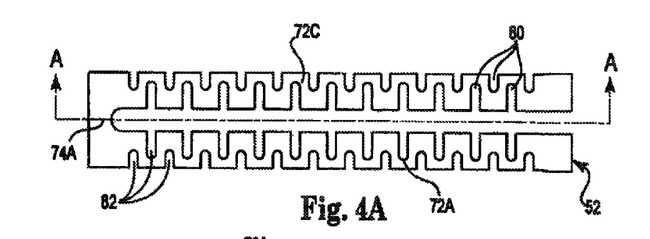
FIG. 4A is a vertical cross-sectional view of the inner sleeve of FIG. 3.
Figure 4B:
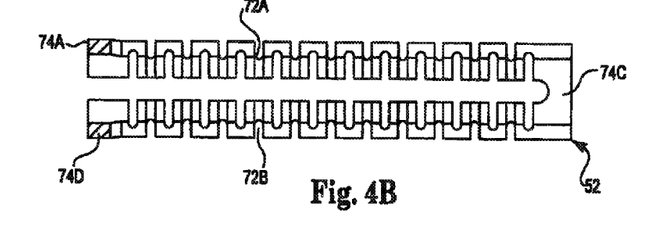
FIG. 4B is a horizontal cross-sectional view of the inner sleeve of FIG. 3.

FIG. 4A is a top view of the inner sleeve 52 of FIG. 3. FIG. 4B is a side view of a vertical section of the inner sleeve 52 taken through deflection region 74A, 74D. In one embodiment, the beams 72 can deflect in pairs, such a for example, beams 72A, 72B may simultaneously deflect around deflection regions 74A, 74D. The deflection can be one or more of linear or rotary displacement, bending, twisting, or a combination thereof. The deflection preferably encompasses at least three degrees of freedom.

Figure 8:
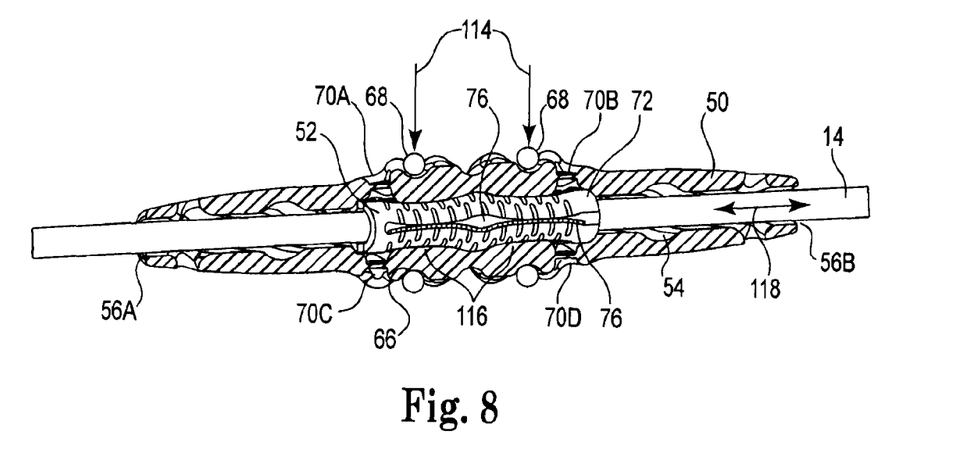
FIG. 8 is a sectional view of the anchor of FIG. 2 compressed onto a therapy delivery element with sutures in accordance with an embodiment of the present disclosure.

Each beam 72 includes a plurality of locations of weakness 80 that facilitate localized deformation (see e.g., FIG. 8). The localized deformation is preferably plastic, but can also be elastic, or a combination of elastic and plastic deformation. In the illustrated embodiment, the locations of weakness 80 are a plurality of slits 82 extending through the beams 72. As used herein, "location of weakness" refers to any discontinuity in a beam structure that facilitates localized deformation, such as for example, slits, holes, recesses, regions thinning, and the like. The deformation can be one or more of linear or rotary displacement, deflection, bending, twisting.

Figure 5:
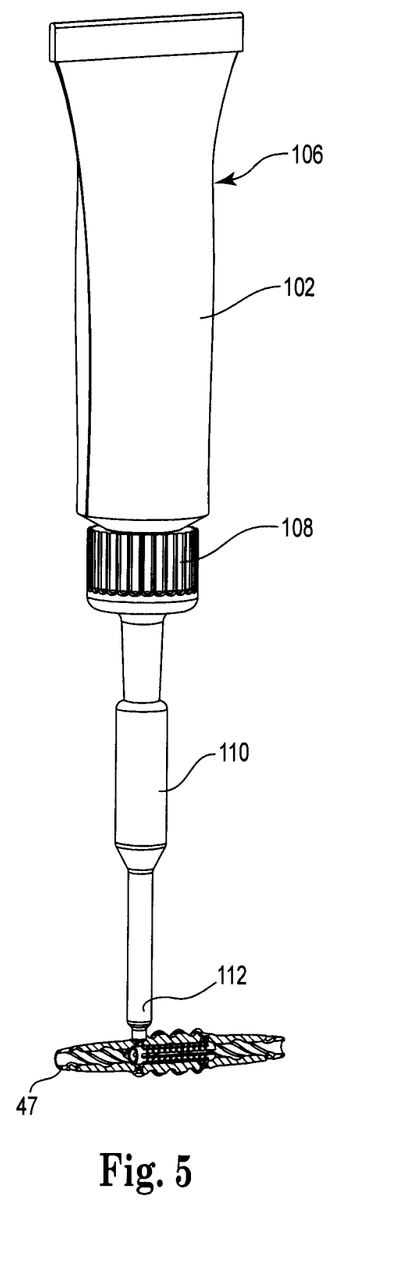
FIG. 5 illustrates an adhesive reservoir coupled to the anchor of FIG. 2 in accordance with an embodiment of the present disclosure.
Figure 6:
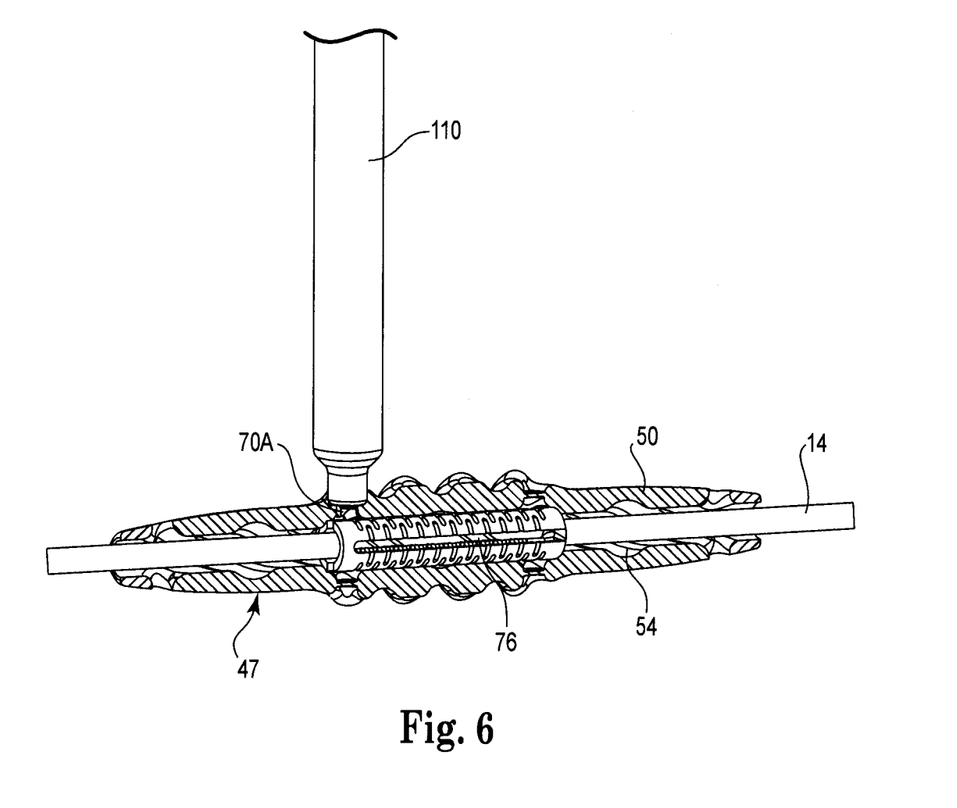
FIG. 6 is an enlarged view of a fill tube coupled to the anchor of FIG. 2.

FIGS. 5 and 6 illustrate an embodiment in which anchor 47 is infused with medical adhesive 102 after the anchor 47 is positioned in the desired location along the therapy delivery element 14. The medical adhesive 102 is located in dispenser 106. Dispenser 106 includes adaptor 108 with a fill tube 110 and a coupling 112 configured to engage with fill port 70A on outer sleeve 50. In one embodiment, the coupling 112 and the fill ports 70 include complimentary threats. Because the medical adhesive 102 is applied after the anchor 47 is prepositioned on the therapy delivery element 14, better bonding results. Moreover, there is no need to slide the anchor 47 into place after the adhesive 102 is applied.

Figure 7:
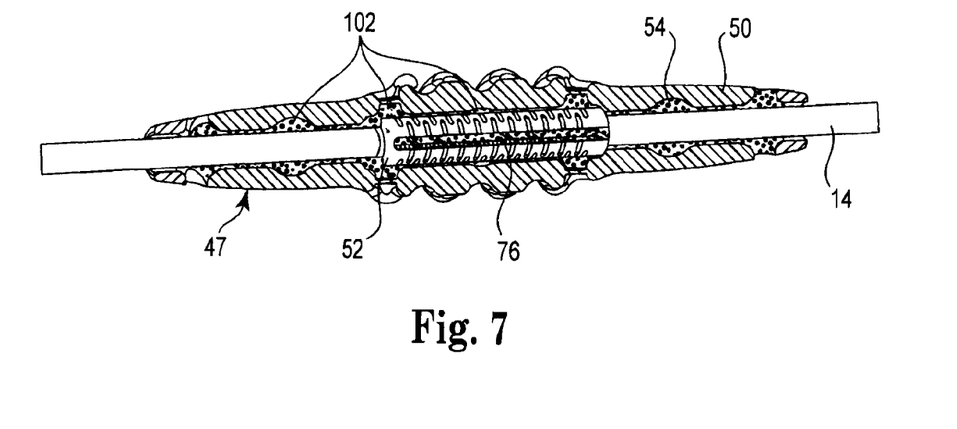
FIG. 7 is a sectional view of a therapy delivery element positioned in the anchor of FIG. 2.

In the embodiment illustrated in FIG. 7, the anchor 47 is infused with the medical adhesive 102 before the sutures 68 are applied. The uncompressed lumens 54, 76 permits the medical adhesive 102 to flow into and around inner sleeve 52.

Before the medical adhesive cures, sutures 68 are wrapped around suture grooves 66 on the outer sleeve 50, as illustrated in FIG. 8. The sutures 68 provide a radially compressive force 114 localized at the suture grooves 66. The sutures 68 also attached the anchor 47 to adjacent tissue in the patient (see FIG. 1). The radially compressive force 114 causes excess adhesive 102 may flow out openings 56A, 56B or the other fill ports 70B, 70C, 70D.

The portion of the lumens 54, 76 and the inner sleeve 52 adjacent to the sutures 68 are compressed. Beams 72 of the inner sleeve 52 are deflected inward, while locations of weakness 80 facilitate localized deformation 116 of the beam 72. The localized deformation 116 increases gripping force 118 between the inner sleeve 50 and the therapy delivery element 14. Once the adhesive 102 cures, the inner sleeve 52 is fixed in the deformed configuration 116 created by the radially compressive force 114.

In an alternate embodiment, the anchor 47 may be used without the medical adhesive 102. In the preferred embodiment, the beams 72 are adapted to deform in at least three degrees of freedom—linear and/or rotary displacement; localized bending, and twisting.

In an alternate embodiment, the medical adhesive 102 may be infused into the anchor 100 after the sutures 68 are applied. See also FIG. 10. The radially compressive force 114 restricts the flow the adhesive 102 within the primary lumen 54, resulting in the adhesive concentrating in the distal end 58A of the outer sleeve 50. In this embodiment, it is desirable to also deliver adhesive 102 through fill ports 70B or 70D so infuse distal end 58B of the outer sleeve 50.

The medical adhesive 102 can be any type of biocompatible medical-grade adhesive. Such medical adhesive includes polyurethane and/or silicone adhesives. One example is Room Temperature Vulcanization (RTV) silicone adhesive which cures at room temperature. This type of adhesive is commercially available in tubes having a threaded neck similar to that shown and described below in reference to FIG. 5. This type of adhesive is generally kept under pressure to prevent it from curing at room temperature. When pressure is removed (e.g., the adhesive is dispensed from the tube) the adhesive will set up, becoming solid, or semi-solid in nature. Another example is a silicone or polyurethane adhesive that cures when exposed to UV or visible light, as is available from the Dymax Corporation.

Figure 9:
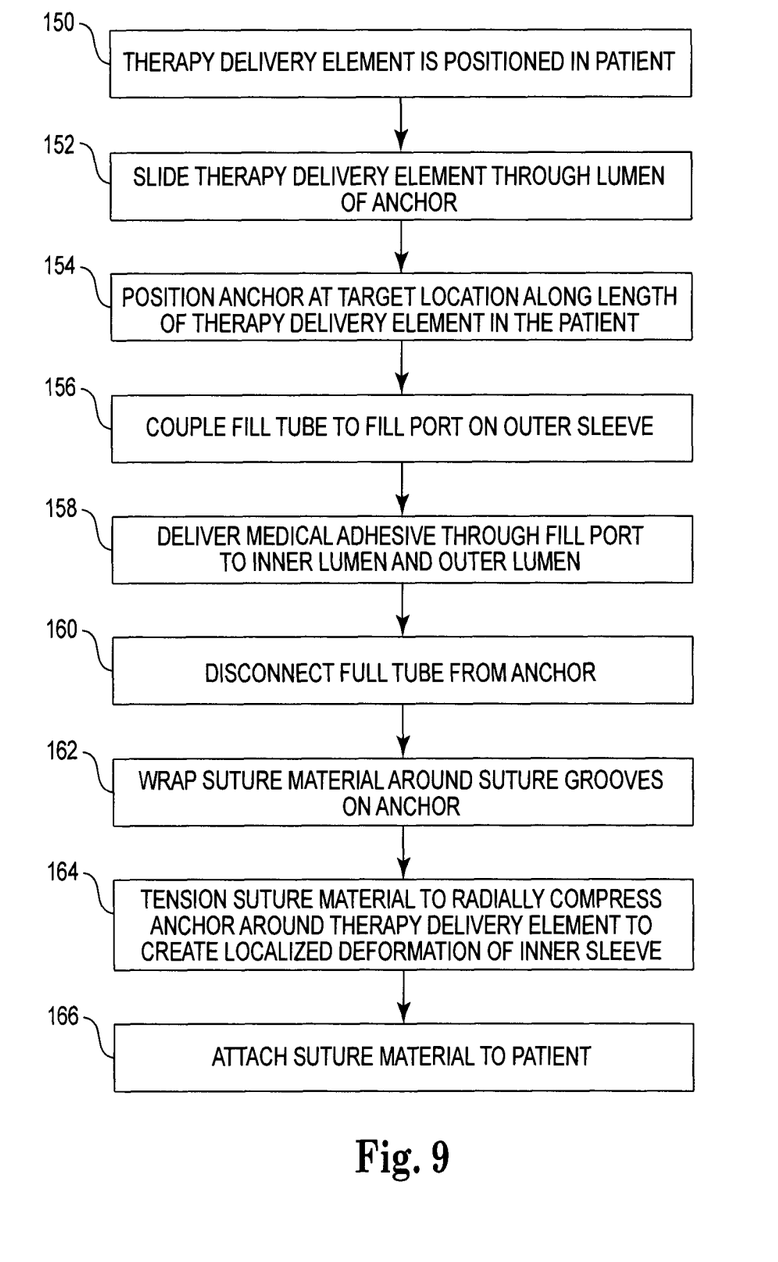
FIG. 9 is a flow chart of a method of using the present anchor in accordance with an embodiment of the present disclosure.

FIG. 9 is a flow diagram of one method in accordance with an embodiment of the present disclosure. The therapy delivery element is first positioned in the patient (150). The proximal end of the therapy delivery element is slid through a lumen of an anchor (152). The anchor is then positioned in the desired location along the therapy delivery element in the patient (154). A dispenser is coupled to a fill port on the anchor (156). A medical adhesive is delivered into the anchor (158). The fill tube on the dispenser is detached from the anchor (160). A suture material is wrapped around suture grooves on the anchor (162). The suture material is tensioned to provide a radially compressive force to the anchor to create localized deformation of an inner sleeve (164). The suture material is also attached to the patient (166).

Figure 10:
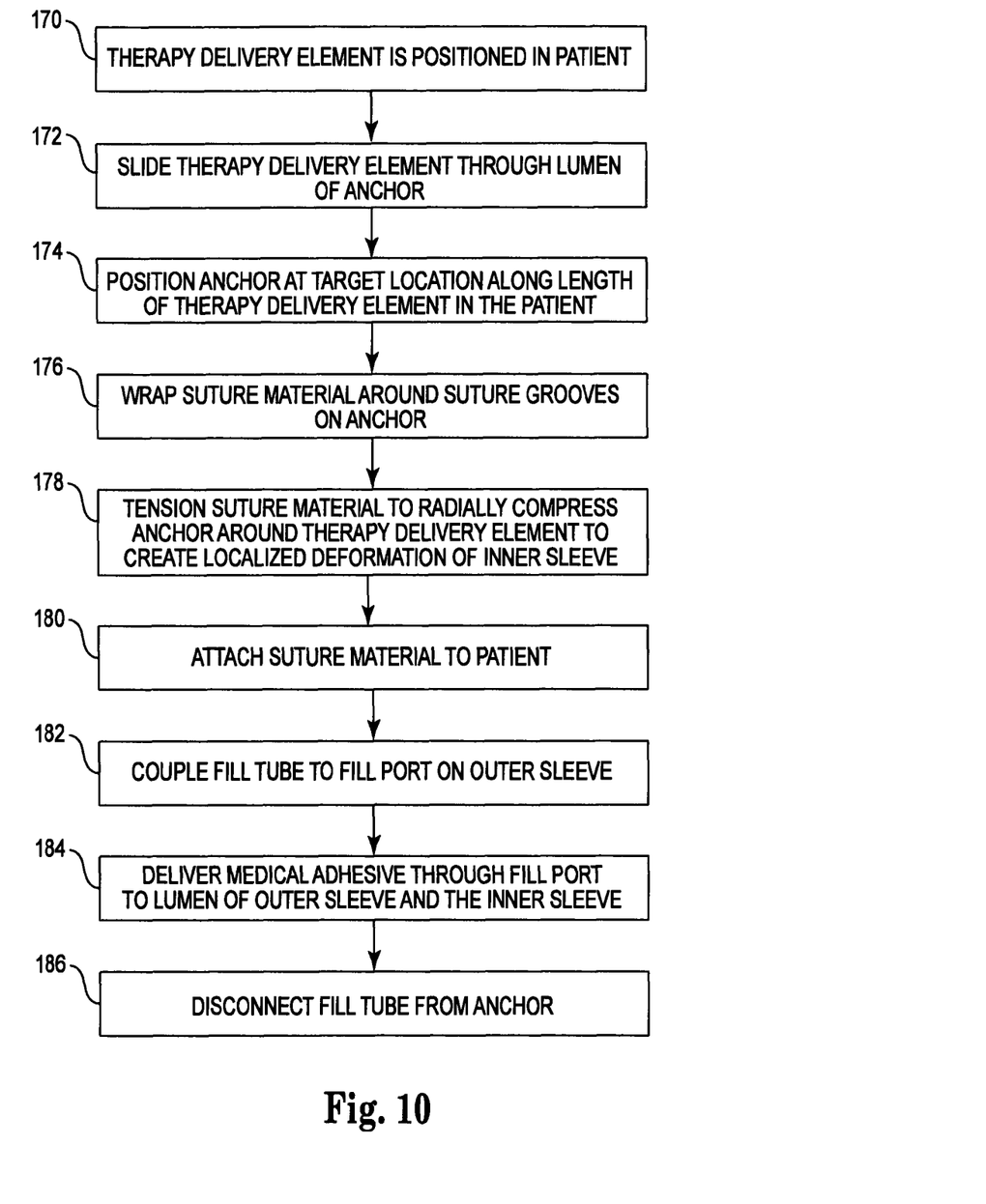
FIG. 10 is a flow chart of an alternate method of using the present anchor in accordance with an embodiment of the present disclosure.

FIG. 10 is a flow diagram of an alternate method in accordance with an embodiment of the present disclosure. The therapy delivery element is first positioned in the patient (170). The proximal end of the therapy delivery element is slid through a lumen of an anchor (172). The anchor is then positioned in the desired location along the therapy delivery element in the patient (174). A suture material is wrapped around suture grooves on the anchor (176). The suture material is tensioned to provide a radially compressive force to the anchor to create localized deformation of an inner sleeve (178). The suture material is also attached to the patient (180). A dispenser is coupled to a fill port on the anchor (182). A medical adhesive is delivered into the anchor (184). The fill tube on the dispenser is detached from the anchor (186).

Figure 11:
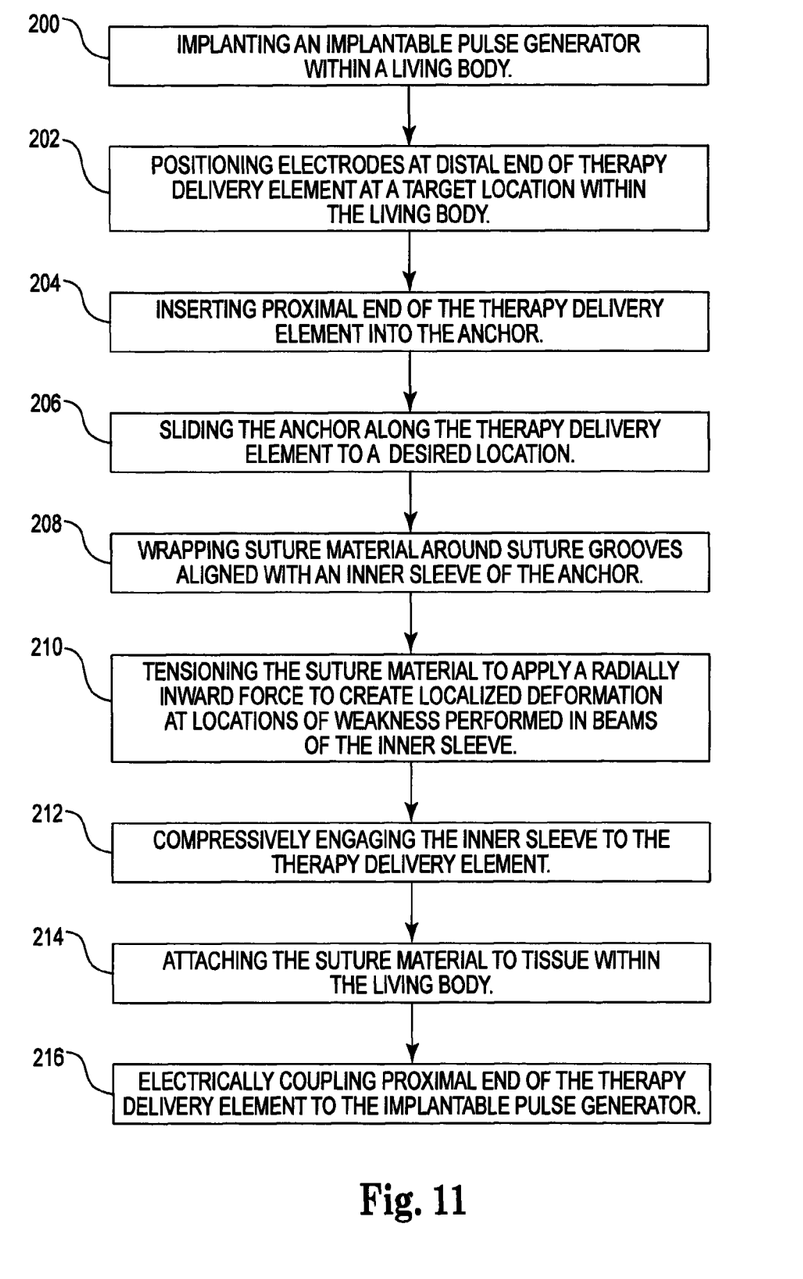
FIG. 11 is a flow chart of a method of implanting a therapy delivery system using the present anchor in accordance with an embodiment of the present disclosure.

FIG. 11 is a flow diagram of a method of implanting a therapy delivery system in accordance with an embodiment of the present disclosure. The method includes the steps of implanting an implantable pulse generator within the living body (200). Electrodes at a distal end of a therapy delivery element are positioned at a target location within the living body (202). A proximal end of the therapy delivery element is inserted into lumens in the present anchor (204). The anchor is slid along the therapy delivery element to a desired location (206). A suture material is wrapped around at least one suture groove aligned with the inner sleeve that is formed in an outer surface of the outer sleeve (208). A radially inward force is applied at the suture groove by tensioning the suture material (210). The radially inward force creates localized deformation at locations of weakness preformed in beams of the inner sleeve. The inner sleeve compressively engages the therapy delivery element (212). The suture material attaches the anchor to tissue within the living body (214). The proximal end of the therapy delivery element is electrically coupled to the implantable pulse generator (216).

Figure 12:
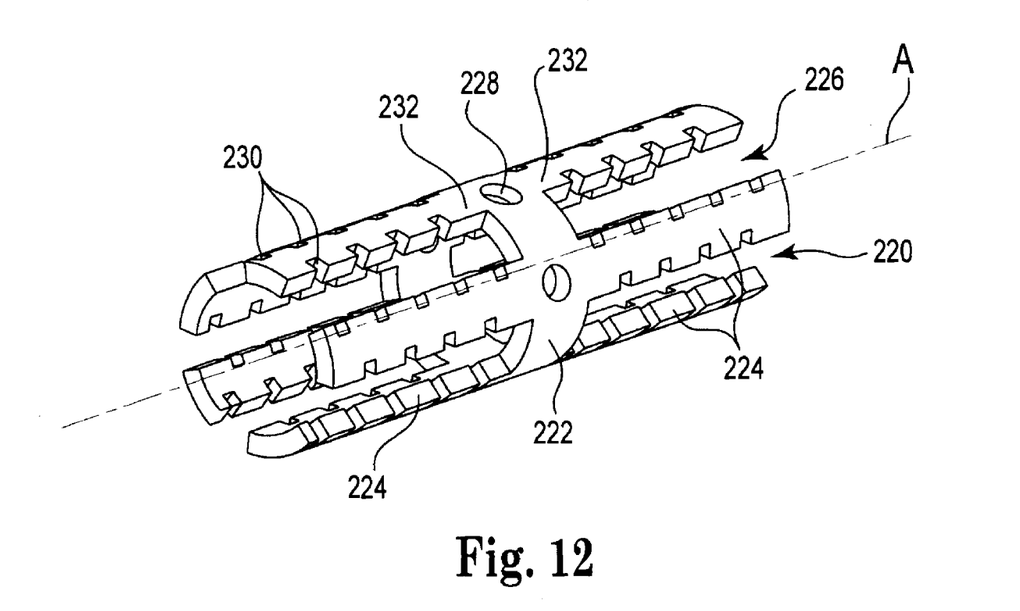
FIG. 12 is a perspective view of an alternate inner sleeve in accordance with an embodiment of the present disclosure.

FIG. 12 is a perspective view of an alternate inner sleeve 220 in accordance with an embodiment of the present disclosure. Center ring 222 includes a plurality of cantilevered beams 224 arranged parallel to the center axis A and concentric with secondary lumen 226. Holes 228 are provided to facility the flow of adhesive and/or deformation of the center ring 222. Attachment points 232 facilitate rotation displacement and twisting of the beams 224 relative to the center ring 222.

Each of the beams 224 preferably includes a plurality of locations of weakness 230 that facilitate localized deformation. The localized deformation can be one or more of bending, twisting, elongation, compression, or a combination thereof.

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. An anchor for securing a therapy delivery element to a desired location within a living body, the anchor comprising:
   a deformable outer sleeve comprising a primary lumen extending along an axis, and an outer surface with a plurality of suture grooves oriented substantially concentric to the axis;
   an inner sleeve comprising a plurality of beams connected at deflection regions arranged around a secondary lumen, the inner sleeve located in the primary lumen adjacent to the suture grooves so that the secondary lumen is substantially concentric with the primary lumen, wherein the inner sleeve is fixed within the primary lumen of the outer sleeve; and
   a plurality of locations of weakness in each of the beams that facilitate localized deformation of the inner sleeve in response to a radially inward force applied around the suture grooves by a suture material, the plurality of locations of weakness including a plurality of slits extending part-way through a beam width from both a first beam edge and a second beam edge, wherein the slits alternate from extending into the beam width from the first edge to extending from the second edge without being in open communication with each other as the slits extend along the length of the beam, wherein the inner sleeve buckles at the slits in response to the radially inward force to grip the therapy delivery element disposed within the inner sleeve.

2. The anchor of claim 1, wherein the outer sleeve comprises distal portions extending beyond the inner sleeve.

3. The anchor of claim 1, wherein at least a portion of the primary lumen comprises grooves adapted to receive a medical adhesive.

4. The anchor of claim 1, wherein the outer sleeve comprises one or more fill ports adapted to direct a medical adhesive to at least the primary lumen.

5. The anchor of claim 1, wherein the outer sleeve comprises at least one fill port with a connector to receive a dispenser containing a medical adhesive.

6. The anchor of claim 1, wherein the inner sleeve comprises a material that plastically deforms in response to the radially inward force.

7. The anchor of claim 1, wherein the inner sleeve comprises one of a thermoplastic material, stainless steel, or Nitinol.

8. The anchor of claim 1, wherein the locations of weakness comprise discontinuities in the beams, including one or more of holes, recesses, or regions thinning.

9. The anchor of claim 1, wherein the localized deformation comprises one or more of bending, twisting, elongation, compression, or a combination thereof.

10. An anchor for securing a therapy delivery element to a desired location within a living body, the anchor comprising:
a deformable outer sleeve including:
a primary lumen extending along an axis; and
an outer surface including a suture groove oriented substantially concentrically to the axis;
an inner sleeve including a plurality of beams connected at deflection regions arranged around a secondary lumen, the inner sleeve located in the primary lumen adjacent to the suture groove so that the secondary lumen is substantially concentric with the primary lumen, wherein the inner sleeve is fixed within the primary lumen of the outer sleeve; and
a plurality of locations of weakness in each of the beams that facilitate localized deformation of the inner sleeve in response to a radially inward force applied around the suture grooves by a suture material, the plurality of locations of weakness including a plurality of slits extending part-way through a beam width from both a first beam edge and a second beam edge, wherein the slits alternate from extending into the beam width from the first edge to extending from the second edge without being in open communication with each other as the slits extend along the length of the beam, wherein the inner sleeve buckles at the slits in response to the radially inward force to grip the therapy delivery element disposed within the inner sleeve.

11. The anchor of claim 10, wherein the outer sleeve includes distal portions extending beyond the inner sleeve.

12. The anchor of claim 10, wherein at least a portion of the primary lumen includes a medical adhesive receiving groove.

13. The anchor of claim 10, wherein the outer sleeve includes a fill port adapted to direct a medical adhesive to at least the primary lumen.

14. The anchor of claim 13, wherein the outer sleeve includes more than one fill port.

15. The anchor of claim 13, wherein the fill port is fluidly coupled to a medical adhesive receiving groove of the primary lumen.

16. The anchor of claim 13, wherein the fill port includes a connector configured to receive a medical adhesive dispenser.

17. An anchor for securing a therapy delivery element to a desired location within a living body, the anchor comprising:
a deformable outer sleeve including:
a primary lumen extending along an axis; and
an outer surface including a suture groove oriented substantially concentrically to the axis; and
an inner sleeve disposed within the outer sleeve adjacent the suture groove of the outer surface, the inner sleeve being fixed within the primary lumen of the outer sleeve, the inner sleeve including at least two beams and a location of weakness within at least one of the beams configured to facilitate localized deformation of the inner sleeve in response to a radially inward force applied around the suture grooves by a suture material, the location of weakness including at least a first slit and a second slit each extending part-way through a beam width, wherein the first slit extends into the beam width from a first edge and the second slit extends into the beam width from a second edge without being in open communication with each other, wherein the inner sleeve buckles at the location of weakness in response to the radially inward force to contact the therapy delivery element disposed within the inner sleeve.

18. The anchor of claim 17, wherein the at least two beams includes a plurality of beams circumferentially disposed around and defining a secondary lumen of the inner sleeve, wherein a pair of adjacent beams of the plurality of beams are circumferentially connected at a deflection region, the pair of adjacent beams of the plurality of beams being otherwise separated from one another by a gap.

19. The anchor of claim 18, wherein the secondary lumen is substantially concentric with the primary lumen.

20. The anchor of claim 17, wherein the first slit and the second slit each extend radially, with respect to the inner sleeve, through the at least one beam from an inner surface to an outer surface of the at least one beam.

21. An anchor for securing a therapy delivery element to a desired location within a living body, the anchor comprising:
a deformable outer sleeve providing a primary lumen extending along a longitudinal axis, the outer sleeve including an outer surface with a plurality of suture grooves oriented substantially concentric to the axis; and
an inner sleeve received in and fixed within the primary lumen of the outer sleeve, the inner sleeve including:
at least four inner beams, each inner beam including a beam width extending from a first edge to a second edge, the beam width being perpendicular to a beam length extending from a beam proximal end to a beam distal end, wherein each beam is spaced from the longitudinal axis;
at least a first proximal deflection portion and a second proximal deflection portion, and at least a third distal deflection portion and a fourth distal deflection portion, wherein proximal ends of the first and second beams are connected at spaced locations to the first proximal deflection portion, distal ends of the second and third beams are connected at spaced locations to the third distal deflection portion, proximal ends of the third and fourth beams are connected at spaced locations to the second proximal deflection portion, and distal ends of the fourth and first beams are connected at spaced locations to the fourth distal deflection portion to thereby create a first axial opening extending from between the fourth and third distal deflection portions and between the first and second beams terminating at the first proximal deflection portion, a second axial opening extending from between the first and second proximal deflection portions and between the second and third beams terminating at the third distal deflection portion, a third axial opening extending from between the third and fourth distal deflection portions and between the third and fourth beams terminating at the second proximal deflection portion, and a fourth axial opening extending from between the second and first proximal deflection portions and between the fourth and first beams terminating at the fourth distal deflection portion; and
a plurality of slits extending part-way through the beam width of each of the inner beams from both the first beam edge and the second beam edge, wherein the slits alternate from extending into the width from the first edge to extending from the second edge without being in open communication with each other as the slits extend along the length of the beam, wherein the inner sleeve buckles at the slits in response to a radially inward force imparted to the outer sleeve to thereby contact a therapy delivery element disposed within the inner sleeve.

22. The anchor of claim 21, wherein each of the plurality of slits extends beyond an imaginary line bisecting the width of a beam and extending from the beam proximal end to the beam distal end.

* * * * *